United States Patent [19]

Blank et al.

[11] Patent Number: 5,081,288

[45] Date of Patent: Jan. 14, 1992

[54] PROCESS FOR THE PREPARATION OF SUBSTITUTED 3,5-DICHLORO-2,4-DIFLUORO-BENZENES

[75] Inventors: Heinz U. Blank, Odenthal; Edwin Ritzer, Burscheid, both of Fed. Rep. of Germany

[73] Assignee: Bayer Aktiengesellschaft, Leverkusen, Fed. Rep. of Germany

[21] Appl. No.: 596,621

[22] Filed: Oct. 10, 1990

Related U.S. Application Data

[63] Continuation of Ser. No. 459,919, Jan. 2, 1990, abandoned, which is a continuation of Ser. No. 278,703, Dec. 1, 1988, abandoned, which is a continuation of Ser. No. 130,830, Dec. 9, 1987, abandoned.

[30] Foreign Application Priority Data

Dec. 11, 1986 [DE] Fed. Rep. of Germany ....... 3642332

[51] Int. Cl.⁵ ................. C07C 263/00; C07C 209/00; C07C 22/00
[52] U.S. Cl. .................................. 560/347; 564/417; 570/147
[58] Field of Search ................ 560/358, 347; 514/741; 570/147; 564/417

[56] References Cited

U.S. PATENT DOCUMENTS 3,294,629 12/1966 Pyne et al. .

Primary Examiner—Alan Siegel
Attorney, Agent, or Firm—Sprung Horn Kramer & Woods

[57] ABSTRACT

Substituted 3,5-dichloro-2,4-difluoro-benzenes of the formula

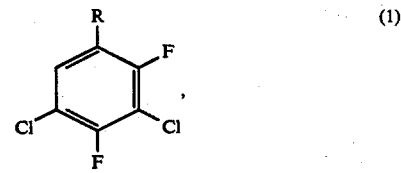

(1)

in which R represents nitro, amino (including the corresponding ammonium salts) or isocyanato, which can be prepared from 2,3,4,5-tetrachloro-nitrobenzene by means of the reaction, carried out initially, with alkali metal fluorides at elevated temperature in a polar, aprotic solvent, starting from a crude 2,3,4,5-tetrachloro-nitrobenzene containing 2,3,5,6-tetrachloro-nitrobenzene and/or 2,3,4,6-tetrachloro-nitrobenzene, and substituted 3,5-dichloro-2,4-difluoro-benzene being isolated from the reaction mixture at the nitro stage or, after reduction of the nitro group, at the amino stage or, after reduction and phosgenation of the amino group, at the isocyanate stage.

10 Claims, No Drawings

PROCESS FOR THE PREPARATION OF SUBSTITUTED 3,5-DICHLORO-2,4-DIFLUORO-BENZENES

This application is a continuation, of application Ser. No. 459,919, filed Jan. 2, 1990, now abandoned, which is a continuation of Ser. No. 278,703, filed Dec. 1, 1988, now abandoned; which is a continuation of Ser. No. 130,830 filed Dec. 9, 1987, now abandoned.

The present invention relates to a process for the preparation of substituted 3,5-dichloro-2,4-difluorobenzenes of the formula

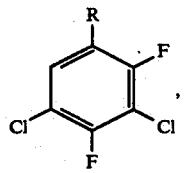

(1)

in which R represents nitro, amino (including the corresponding ammonium salts) or isocyanato, from 2,3,4,5-tetrachloro-nitrobenzene by means of the reaction, carried out initially, with alkali metal fluorides at elevated temperature in a polar, aprotic solvent, which process is characterized in that a crude 2,3,4,5-tetrachloro-nitrobenzene containing 2,3,5,6-tetrachloro-nitrobenzene and/or 2,3,4,6-tetrachloro-nitrobenzene is employed, and substituted 3,5-dichloro-2,4-difluoro-benzene is isolated from the reaction mixture at the nitro stage or, after reduction of the nitro group, the amino stage or, after reduction and phosgenation of the amino group, at the isocyanate stage.

The substances of the formula (I) are intermediates for the preparation of compounds which are active against parasites (U.S. Pat. No. 3,294,629; EP 52,833).

The reaction of 2,3,4,5-tetrachloro-nitrobenzene with potassium fluoride to form 3,5-dichloro-2,4-difluoronitrobenzene in some polar, aprotic solvents has already been described, although the yields were frequently not satisfactory; thus, the reaction was carried out in dimethylsulphoxide (DMSO) in U.S. Pat. No. 3,294,629, in dimethylformamide (DMF) in EP 52,833 and in Gunma Journal of Liberal Arts and Sciences (University of Gunma, Japan) 18 (1984), 55–66, and in dimethylsulphone (DMSO$_2$) in Research Disclosure RD 25,517.

All the processes mentioned start from isomerically pure 2,3,4,5-tetrachloro-nitrobenzene. However, the isolation of pure 2,3,4,5-tetrachloro-nitrobenzene from crude, industrially prepared tetrachloro-nitrobenzene is expensive and high in loss, since the impurities are chemically similar substances which require a great effort for separation.

It was therefore very desirable to employ crude, industrially prepared 2,3,4,5-tetrachloro-nitrobenzene and to obtain 3,5-dichloro-2,4-difluoro-nitrobenzene in an intended purity suitable for further use.

Crude tetrachloro-nitrobenzene can be obtained by chlorination of benzene or partially chlorinated benzenes to the tetrachlorobenzene stage and subsequent nitration of the tetrachlorobenzene fraction using nitrating acid, or by chlorination of nitrobenzene or incompletely chlorinated nitrobenzenes to the tetrachloro-nitrobenzene stage. The starting materials may accordingly be: benzene, chlorobenzene, isomeric dichlorobenzenes and trichlorobenzenes for further chlorination and nitration; crude 1,2,3,4-tetrachlorobenzene for nitration; and nitrobenzene, isomeric chloro-nitrobenzenes, dichloro-nitrobenzenes and trichloro-nitrobenzenes for further chlorination. The use of dichloro- and trichloro-nitrobenzenes in which both ortho-positions to the nitro group are occupied are excepted. However, it must be accepted that such undesired isomers are also produced during processing of industrial mixtures. The same applies to undesired polychlorobenzene isomers.

Crude 2,3,4,5-tetrachloro-nitrobenzene is therefore characterized, above all, in that it contains 2,3,5,6-tetrachloro-nitrobenzene and/or 2,3,4,6-tetrachloro-nitrobenzene. These or their reaction products must therefore be taken into account as undesired by-products in the process according to the invention; they can be represented by the general formulae

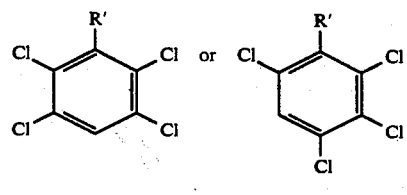

(2)     (3)

in which R' has the meaning of R and, in addition, may represent fluorine.

Whereas undesired by-products of the formula (2) are produced on use of crude tetrachloro-nitrobenzene which is obtained by the two preparation routes described above, by-products of the formula (3) are produced mainly on use of crude tetrachloro-nitrobenzene which is obtained by chlorination of nitrobenzene or incompletely chlorinated nitrobenzenes. In addition, incompletely reacted precursors can be expected in crude tetrachloro-nitrobenzene.

Crude tetrachloro-nitrobenzene via the tetrachlorobenzene stage, and its reaction products, may be considered as an example with reference to the enclosed equation:

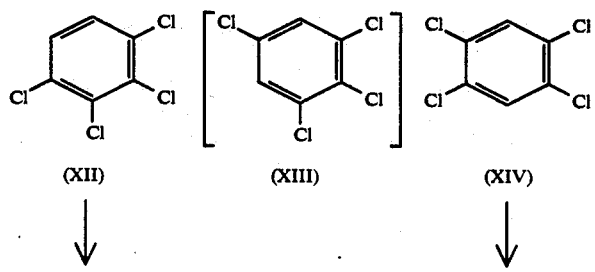

(XII)        (XIII)        (XIV)

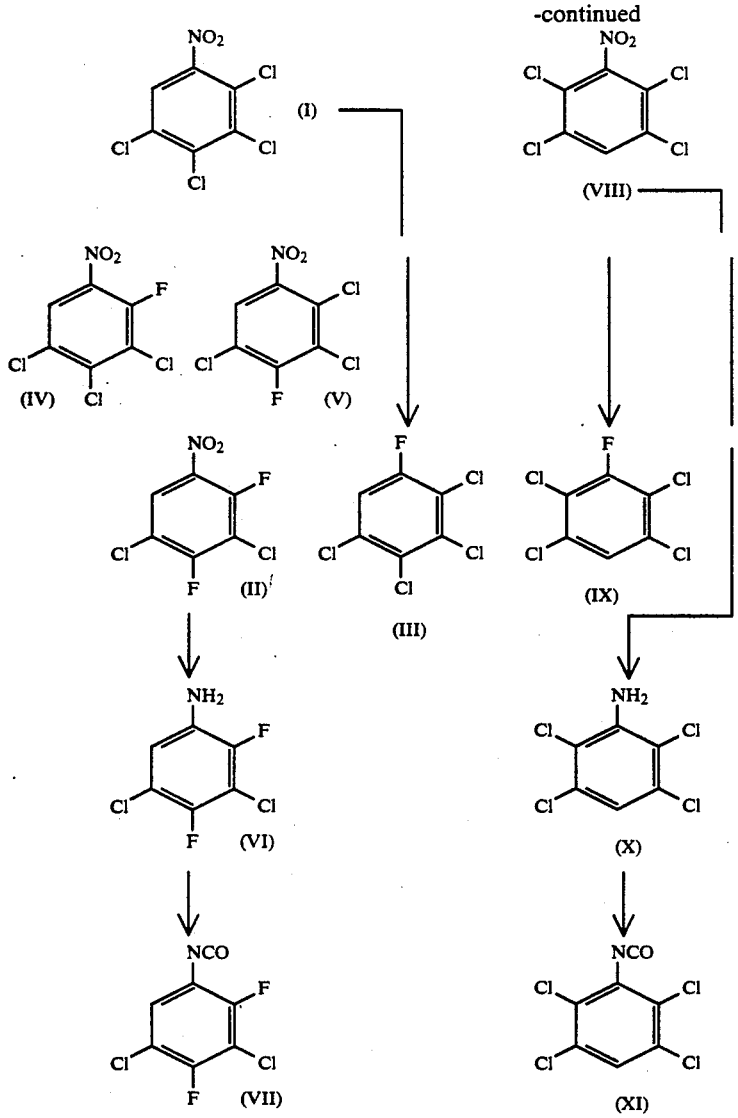

Besides the 1,2,3,4-tetrachlorobenzene (XII) desired, the tetrachlorobenzene fraction contains various, but interfering, amounts of 1,2,4,5-tetrachlorobenzene (XIV), and minor amounts of 1,2,3,5-tetrachlorobenzene (XIII). The amount of 1,2,4,5-tetrachlorobenzene (XIV) varies between 2 and 40% by weight of the total crude tetrachlorobenzene. The tetrachlorobenzene fraction furthermore contains small amounts of pentachloro-benzene and hexachloro-benzene, and possibly also traces of trichlorobenzene.

The impurities mentioned appear at the nitro stage. In the context of the said, mainly the 2,3,4,5-tetrachloronitrobenzene (I) desired and the main impurity 2,3,5,6-tetrachloro-nitrobenzene (VIII) are to be expected here.

In the nucleophilic substitution reaction with alkali metal fluoride, a mixture of the 3,5-dichloro-2,4-difluoro-nitrobenzene (II) desired, the incompletely fluorinated compounds 3,4,5-trichloro-2-fluoro-nitrobenzene (IV) and 2,3,5-trichloro-4-fluoro-nitrobenzene (V), the 2,3,4,5-tetrachloro-fluorobenzene (III), formed by undesired fluorine substitution, the 2,3,5,6-tetrachlorofluorobenzene (IX) originating from (VIII), and unchanged (I) and (VIII) is obtained from the compounds (I) and (VIII) from the nitration stage.

The separation of such a mixture can no longer be carried out in an economically efficient manner. In the case of distillative separation with relatively long thermal load, considerable decomposition can also be expected in the case of such highly substituted substances as those mentioned.

The process according to the invention is based on a number of surprising findings:

a) The (II) desired suffers from decomposition in the case of thermal treatment which is longer than is necessary to achieve the maximum yield. The processes occurring during this decomposition are not known in detail; an autocatalytic process is possibly present.

b) At the same time as the conversion of (I) into (II), the undesired components 2,3,5,6- and 2,3,4,6-tetrachloronitrobenzene ((VIII) and its positional isomer likewise having 2 chlorine substituents in the ortho-positions to the nitro group) in crude tetrachloro-nitrobenzene undergo nucleophilic $NO_2$-F substitution to form 2,3,5,6- and 2,3,4,6-tetrachloro-fluorobenzenes ((IX) and its positional isomer). This $NO_2$-F substitution ("boiling off" of the nitrobenzenes mentioned) proceeds fundamentally more slowly than the desired conversion of (I) into (II).

c) Surprisingly, it was shown that the thermal decomposition according to a) initially, however, starts up only slowly and only accelerates after a relatively long period of heating, so that "boiling off" according to b) can be carried out in order to reduce contamination by the undesired 2,3,5,6- or 2,3,4,6-tetrachloro-nitrobenzenes mentioned to an acceptable level, without the necessity of simultaneously accepting too high losses in yield of (II).

d) That which was not economically efficiently possible in the case of crude tetrachloro-nitrobenzene is now possible after nucleophilic fluorination, namely physical removal of the impurities, mainly in the form of $NO_2$-free fluorobenzenes.

e) In a further embodiment of the process according to the invention, which is described in greater detail below, it was found that removal by physical methods can also be carried out successfully after reduction of the nitro group to the amino stage (VI) or after reduction and phosgenation to the isocyanate stage (VII), a combination of "boiling off" and physical separation only being possible also at one of the subsequent stages. The route to be followed in each case depends on the degree of contamination of crude tetrachloro-nitrobenzene and on the desired degree of residual contamination in (II) or (VI) or (VII).

In order to recognize the findings mentioned under a) to d) and to carry out the process according to the invention, conventional analytical methods, for example gas chromatography, are used. It may turn out here that the content of the undesired tetrachloro-nitrobenzenes mentioned is already reduced sufficiently when the maximum yield of (II) is reached, and that physical removal leads to the desired result. In other cases, the duration of heating of the reaction batch is lengthened and interrupted when the intended, analytically detectable further reduction of the impurities is reached, it being possible for removal of the remaining impurities as early as the nitro stage to be sufficient in some cases.

Of course, when the process according to the invention is carried out regularly, the analytical observation of the reaction batch leads to standardized process parameters, as is also conventional elsewhere in chemical technology.

The nucleophilic fluorination is carried out using an alkali metal fluoride, preferably a heavy alkali metal fluoride, such as potassium fluoride, rubidium fluoride or caesium fluoride, particularly preferably potassium fluoride. An additive, known per se, of alkali metal chloride, for example 0.5-20% by weight, relative to the amount of the alkali metal fluoride, can be added to the alkali metal fluoride. In a preferred fashion, the process is carried out without such an additive.

In the process according to the invention, one or more phase-transfer catalysts, such as tetrabutylammonium bromide, trimethylphenylammonium chloride, triethylbenzylammonium chloride, trimethylbenzylammonium chloride, hexadecyltributylphosphonium bromide and crown ethers (18-crown-6) inter alia, may furthermore be added, for example in an amount of 0.3-30% by weight, relative to the tetrachloro-nitrobenzene to be reacted.

Suitable polar, aprotic solvents are, for example: dimethylsuphoxide (DMSO), dimethylformamide (DMF), dimethyl sulphone ($DMSO_2$), tetramethylenesulphone ($TMSO_2$) sulpholane), acetonitrile, benzonitrile, nitrobenzene, dimethylacetamide, N-methyl-pyrrolidone (NMP), N-methyl-ε-caprolactam, tetramethylurea, hexamethyl-phosphoric acid triamide, diethyleneglycol dimethylether (diglyme) and other compounds which are known to those skilled in the art.

These solvents can also be employed as a mixture. Furthermore, up to 50% by weight, relative to the total amount of solvent, of other inert solvents, such as benzene, toluene, chlorobenzene, dichlorobenzene, trichlorobenzene or tetrachlorobenzene, can be added. In a preferred fashion, the process is carried out in DMSO, DMF or $DMSO_2$, and in a particularly preferred fashion in DMSO.

If the boiling point at atmospheric pressure of the other inert solvent is lower than the intended reaction temperature, the process may also be carried out at increased pressure, for example at 1.5-10 bar. By working at reduced pressure, the temperature can be regulated very well by adjusting the corresponding boiling equilibrium ("evaporative cooling"). However, it is sufficient in most cases to carry out the process at atmospheric pressure.

The process according to the invention is carried out at a temperature of 60°-160° C., preferably 80°-140° C., particularly preferably 95°-125° C. The reaction time is 20-0.2 hours, where longer reaction times must be expected on setting a lower temperature, and vice versa. The abovementioned optimized temperature/time relationships for the formation of (II) are somewhat different for the solvents specified, but can be determined by those skilled in the art by means of simple preliminary experiments. Thus, for example, it has been found that, for the solvent DMSO, the temperature and time are linked by the relationship $T\ (°C.) = A - 33\ \log\ t(h)$, in which A assumes values of 100-137, preferably 110-135, particularly preferably 115-130. This minimum time for the process according to the invention can be extended, depending on the desired degree of residual contamination.

By following the reaction batch analytically, in particular beyond the optimized time, at a prespecified temperature, for the formation of (II), the degree of residual contamination by (VIII) is determined, so that standardized process parameters, in particular temperature and time, can be worked out when the process is carried out repeatedly.

The molar tetrachloro-nitrobenzene:alkali metal fluoride:polar aprotic solvent ratio in the process according to the invention generally extends from 1:2:1 to 1:6:30, preferably from 1:2.2:2.4 to 1:4.4:10. When DMSO is used, the values in the lower part of the range, namely from 1:2.2:2.0 to 1:5:24, preferably 1:2.3:2.4 to 1:4.0:10, particularly preferably 1:2.4:2.8 to 1:3.2:4.6, can be maintained. These favourable values are limited, in the direction of relatively high solids contents in the suspension in DMSO, only by decreasing stirrability of the suspension. By means of such high solids contents, a considerably increased space/time yield and a considerable saving in energy can be achieved.

The alkali metal fluoride and the polar, aprotic solvent employed are employed in anhydrous form. For this purpose, the alkali metal fluoride can be pretreated by spray-drying or dried for some time at up to 600° C. The solvent is dried in a known form over phosphorus pentoxide or other known drying agents. If possible, the solvent can also be freed from water by simple distillation; a further possibility comprises adding toluene or another azeotrope-former and removing the water as an azeotrope by distillation.

In the case of the particularly preferred use of DMSO as the polar, aprotic solvent, very drastic drying methods are not necessary in a particularly favourable fashion. Thus, for example, an alkali metal fluoride which has been dried in a drying oven at 200° C./200 torr can be used; it is even possible to use commercially available dry alkali metal fluorides.

In general, the polar, aprotic solvent, or a mixture containing such a solvent, and the alkali metal fluoride are presented and, if necessary, subjected to drying by azeotropic distillation. The intended reaction temperature is in many cases already reached during this procedure. The crude 2,3,4,5-tetrachloro-nitrobenzene is then added to the suspension of the alkali metal fluoride in the polar, aprotic solvent; this addition can take place after the reaction temperature is reached or before or during the heating phase. As long as a reaction time which is optimized for the formation of (II) is passed through at the selected reaction temperature before following the reaction batch analytically, the reaction time commences when the reaction temperature is reached. In the case of relatively large batches on an industrial scale, it may be desirable to add the starting material in portions; in any case, the addition of a relatively large amount of a starting material requires a suitable handling time, which is known to those skilled in the art of chemical process technology. In such a case, the commencement of the reaction time is set at the end of the addition.

When the nucleophilic fluorination is complete, the resultant reaction mixture can be worked up in various fashions. Thus, the inorganic salts (alkali metal fluorides/chlorides) are firstly separated off, for example filtered off or centrifuged off, in general after the reaction mixture is cooled. Further separation into solvent and reaction products can then be carried out by distillation, extraction or other physical separation methods, such as column chromatography. Furthermore, water can be added to the solution of the fluorinated reaction products in the polar, aprotic solvents, and the fluorinated reaction products precipitate, can be separated off and can be fed to further, optional work-up and purification.

In a particularly advantageous variant, the solution of the fluorinated reaction products in the polar, aprotic solvent can be extracted batchwise or continuously, in preferred fashion continuously, with one or more straight-chain or branched, open-chain or cyclic aliphatic hydrocarbons which have a boiling point of at least 30° C. During this extraction, the fluorinated reaction products pass over into the aliphatic hydrocarbon phase and can be obtained therefrom by at least partial evaporation of the aliphatic hydrocarbons and are fed, if appropriate, to further fine purification. The polar, aprotic solvent freed from the fluorinated reaction products by extraction can be fed to the next reaction batch in the process according to the invention as such without further work-up. Suitable extraction apparatuses for this specific process variant are known to those skilled in the art, for example extractors for lower-density extracting agents according to Ludwig (DE-AS (German Published Specification) 2,221,544). Aliphatic hydrocarbons for this process variant are, for example, pentane, hexane, octane, decane, dodecane, hexadodecane, cyclohexane, methylcyclohexane, methylcyclopentane, isooctane, mixtures of these aliphatic hydrocarbons and the aliphatic distillation cuts petroleum ethers having boiling ranges 30°-50° C., about 40° C., 40°-60° C., 60°-70° C., 40°-80° C., light petroleum (60°-95° C.), ligroin (80°-110° C.), soldering benzine (60°-140° C.), petroleum benzine (100°-140° C.) and others.

The fluorinated reaction products can be separated physically after removal of the polar, aprotic solvent. Such physical methods are distillation, if appropriate under reduced pressure, fractional crystallization and column chromatography. It is possible, in particular through the latter method, to remove substances without a nitro group, such as (III) and (IX), from the nitro products. The desired (II) can subsequently be separated from undesired tetrachloro-nitrobenzenes by a conventional method, for example by distillation.

Further processing of (II) to give compounds which are active against parasites is carried out via the amino compound (VI) which is derived from the nitro compound. For this purpose, (II), for example in solution in the aliphatic hydrocarbons from the extraction or, after other isolation of (II), alternatively in alcohols or other suitable solvents which are known to those skilled in the art, is hydrogenated catalytically on noble metal catalysts, Raney metals or other hydrogenation catalysts. In principle, for example, reduction of the nitro group to the amino group using iron/acid is also possible. The compounds without nitro groups present in the hydrogenation mixture, for example (III) and (IX), behave inertly during this hydrogenation. When the hydrogenation is complete, the amino compound (VI) with the remaining acceptable amounts of contamination by tetrachloro-anilines are precipitated as a salt by addition of a mineral acid, such as sulphuric acid, phosphoric acid or hydrogen halide, preferably hydrogen halide, and can thus be separated from compounds without an amino group, such as (III) and (IX). The column chromatography described in connection with the nitro compound (II) thus becomes superfluous, which represents a further cost saving.

A mixture thus prepared of (VI) and tetrachloroanilines can furthermore be micropurified by the above-mentioned physical methods, for example by vacuum distillation, the salts, if appropriate, being converted back into the free aniline compounds. The separation, for example distillative, of only these few remaining compounds is essentially more likely to succeed and therefore more inexpensive than use of the physical methods and one of the previous stages with a mixture of many compounds. Such a fine distillation can be combined with the conversion, occurring according to the invention, of 2,3,5,6- or 2,3,4,6-tetrachloro-nitrobenzenes into the corresponding tetrachloro-fluorobenzenes, and thus represents an interesting embodiment of the process according to the invention, by "boiling off" only part of these tetrachloro-nitrobenzenes to form the tetrachloro-fluorobenzenes, whereas another part is removed distillatively at the aniline stage. In particular, when large amounts of 2,3,5,6- or 2,3,4,6-tetrachloronitrobenzenes are to be removed, preference is given to removing only a minor part of these by "boiling off" and removing the major part by distillation at the aniline stage or at one of the further subsequent stages mentioned above, whereas, in the case of relatively small amounts of 2,3,5,6- or 2,3,4,6-tetrachloro-nitrobenzenes, these are reduced to an acceptable level merely by the "boiling off" mentioned. Depending on the degree of contamination of the crude tetrachloronitrobenzene, the desired permitted content of residual contamination can thereby be produced without having to accept largescale decomposition of (II) and thus a reduction in yield.

The tetrachloro-fluorobenzenes (III) and (IX) remaining during the removal of the anilines (VI) and (X) via their salt form can be obtained separately and fed to their own use.

In a very similar fashion, the mixture of the anilinium salts removed can be phosgenated in a fashion which is known in principle to those skilled in the art; the mixture resulting therefrom of the isocyanate (VII) with tetrachlorophenyl isocyanates can then be resolved into the isocyanates mentioned, which have a higher purity than previously, by means of the abovementioned physical methods, for example by distillation. In this variant also, part of the intended degree of residual contamination can thus be achieved by "boiling off", whereas further reduction in residual contamination is achieved, for example, by distillation at the isocyanate stage.

EXAMPLE 1

In all illustrative embodiments, the compounds mentioned with Roman numerals relate to the equation above.

A crude tetrachloro-nitrobenzene containing 78.0% of (I) and 9.2% of (VIII) was used; the remainder essentially comprised tetrachlorobenzene, pentachlorobenzene and hexachlorobenzene. 26.1 g of this crude tetrachloronitrobenzene were heated to 120° C. with 15.1 g of commercially available potassium fluoride which had not been further pretreated, and 39 g of DMSO, and the reaction was followed analytically at the time intervals given in the table by analysing the composition, by gas chromatography, of the samples withdrawn.

TABLE

| | Composition, determined by gas chromatography, of the reaction mixture (% by weight) | | | | |
|---|---|---|---|---|---|
| t (h) | II | III | IX | VIII | I |
| 1 | 35.0 | 3.9 | 2.4 | 8.4 | 16.0 |
| 2 | 54.0 | 4.9 | 4.1 | 6.9 | 5.5 |
| 4 | 61.5 | 5.1 | 5.2 | 5.7 | 2.2 |
| 6 | 65.6 | 5.9 | 8.2 | 3.0 | 1.1 |
| 8 | 59.5 | 6.6 | 10.2 | 0.9 | 0.9 |
| 12 | 54.9 | 7.1 | 10.9 | 0.8 | 1.3 |
| 16 | 51.4 | 7.9 | 11.9 | 1.0 | 1.7 |
| 20 | 47.9 | 8.3 | 12.8 | 0.8 | 1.7 |

The components missing up to 100% by weight are distributed amongst tetrachlorobenzene, pentachlorobenzene and hexachlorobenzene, at relatively short reaction times, amongst only partially reacted (IV) and (V), and, furthermore at long reaction times, amongst unknown decomposition products. This increased decomposition at a relatively long reaction time permits the amount of (III) and the sum of (VIII) and (IX) to increase relatively whilst the amount of (II) and all the reaction products becomes smaller in absolute terms.

In a repetition of the experiment described, the reaction was interrupted after a running time of 8 hours, and the reaction products obtained in this reaction were extracted with cold hexane in a 300 ml Ludwig rotation perforator for liquid-liquid extraction with specifically lighter solvents (German Auslegeschrift 2,221,554) to Normag). After the hexane phase obtained was washed once with 100 ml of water, 2 g of Raney nickel/iron as hydrogenation catalyst were added. Hydrogenation was subsequently carried out at 50° C. and an $H_2$ pressure of 10 bar until the take-up of hydrogen had ceased. After filtering off the hydrogenation catalyst, HCl gas was passed into the hexane phase, whereupon (VI) deposited in crystalline form as the hydrochloride. After filtration and after washing with cold n-hexane, 17.7 g of (VI.HCl) having a purity of 99% were obtained.

EXAMPLE 2

A crude tetrachloro-nitrobenzene containing 82% by weight of (I) (the remainder to 100% comprised 8.9% by weight of (VIII) and otherwise essentially tetra-pent- aand hexachlorobenzene) was used. 130 g of this crude tetrachloro-nitrobenzene were suspended with 75.5 g of KF in 150 g of DMSO, and the mixture was warmed at 120° C. for 4 hours. After cooling to room temperature, the KF/KCl solids mixture was filtered off through a suction filter and washed twice with 30 ml of DMSO in each case. The DMSO solution obtained was subsequently extracted with n-hexane in the fashion described in Example 1. According to analysis by gas chromatography, the reaction mixture contained
71.0% of (II)
5.5% of (III)
6.3% of (IX)
1.4% of pentachlorobenzene
2.8% of (VIII)
0.5% of (I).

EXAMPLE 3

130 g of the crude tetrachloro-nitrobenzene employed in Example 2 were warmed to 135° C. for 16 hours in 200 g of $DMSO_2$ with 75.5 g of KF. The mixture was subsequently allowed to cool to 120° C., and 250 ml of toluene were slowly added; during this addition, the temperature fell further and $DMSO_2$ crystallized out. After further cooling to 10° C. for one hour, the solids ($DMSO_2$, KF and KCl) were filtered off under suction and washed twice with 100 ml in each case of cold toluene at 0° C. The filter cake was washed twice with 100 ml of 0.1N HCl (about 3.7% by weight) in each case and twice with 100 ml of 3% strength aqueous soda solution in each case. The toluene phase was concentrated to dryness in vacuo. 94.8 g of an oil were obtained as a crude product. Analysis by gas chromatography gave the following contents:
73.1% of (II)
3.6% of (III)
8.2% of (IX)
1.6% of pentachlorobenzene
1.2% of (VIII)
3.2% of (XIV)
2.1% of (XII)

EXAMPLE 4

Example 2 was repeated with a reaction time of only 2 hours. Analysis by gas chromatography gave the following contents in the reaction mixture:
60.0% of (II)
4.7% of (III)
5.1% of (IX)
2.5% of (XIV)
2.9% of (XII)
1.3% of pentachlorobenzene
5.6% of (VIII)
2.5% of (I)

EXAMPLE 5

Example 2 was repeated with the exception that the pressure was adjusted to 100 mbar. This produced an internal temperature of 120° C. which could be controlled by evaporative cooling. Analysis of the reaction mixture by gas chromatography gave the following contents:

69.2% of (II)
5.8% of (III)
5.6% of (IX)
2.4% of (XIV)
3.1% of (XII)
1.2% of pentachlorobenzene
3.9% of (VIII)
0.7% of (I)

EXAMPLE 6

The procedure as in Example 2 was carried out, but the reaction time was only 3 hours. KF was employed without further pretreatment. Analysis of the reaction mixture by gas chromatography gave the following contents:

61.5% of (II)
5.2% of (III)
5.1% of (IX)
2.6% of (XIV)
3.3% of (XII)
1.4% of pentachlorobenzene
5.7% of (VIII)
2.2% of (I)

The examples described latterly show the production of different degrees of purity of (II) by varying the reaction parameters.

EXAMPLE 7

Example 5 was repeated. The reaction products were extracted from the solution in DMSO with n-hexane, as was described in Example 1. The reaction mixture was catalytically hydrogenated in n-hexane, likewise according to the description above; the substituted anilines formed were precipitated as the hydrochloride. These aniline hydrochlorides, separated from the remaining solution, were converted into the corresponding isocyanates using phosgene. For this purpose, 90 g of an aniline hydrochloride mixture containing 95.0% by weight (0.37 mole) of (VI) and 4.9% by weight (0.02 mole) of (X) were suspended in 400 ml of toluene, and 60 g (0.6 mole) of phosgene were passed in at room temperature, the mixture was heated slowly to 100° C., and this temperature was held for 5 hours. After blowing out the phosgene using a stream of $N_2$, the toluene was removed by distillation, and the isocyanates thus obtained were separated by distillation. (VII) was obtained on distillation at 24 mbar and 112° C. After cooling the distillation residue and further reducing the pressure to 1 mbar, the commencement of gentle sublimation was observed at 50° C. It was then possible to obtain (XI) in a satisfactory fashion by sublimation at 120° C./1 mbar.

We claim:

1. Process for the preparation of substituted 3,5-dichloro-2,4-difluoro-benzenes of the formula

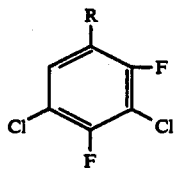

in which R represents nitro, amino (including the corresponding ammonium salts) or isocyanato, carried out initially, with alkali metal fluorides at elevated temperature in a polar, aprotic solvent, wherein a crude 2,3,4,5-tetrachloro-nitrobenzene containing 2–40% by weight of the total crude tetrachlorobenzene of 2,3,5,6-tetrachloro-nitrobenzene and/or 2,3,4,6-tetrachloro-nitrobenzene is employed and the substituted 3,5-dichloro-2,4-difluorobenzene is isolated from the reaction mixture at the nitro stage or, after reduction of the nitro group, at the amino stage or, after reduction and phosgenation of the amino group, at the isocyanato stage and the reaction, carried out initially is carried out at a temperature of 60°–160° C., and a reaction time of 20–0.2 hours in a fashion such that the undesired 2,3,5,6-tetrachloro-nitrobenzene is converted into 2,3,5,6-tetrachloro-fluorobenzene and/or the undesired 2,3,4,6-tetrachloro-nitrobenzene is converted into 2,3,4,6-tetrachloro-fluorobenzene to the desired degree of residual contamination, the reaction mixture is cooled and separated into the alkali metal fluorides/chlorides, the solvent and the reaction products, and the 3,5-dichloro-2,4-difluorobenzene is then separated physically from the conversion products of 2,3,5,6-tetrachloro-nitrobenzene and/or 2,3,4,6-tetrachloro-nitrobenzene at the nitro stage, the amino stage or the isocyanato stage.

2. Process according to claim 1, wherein the initial reaction is carried out at a temperature of 80°–140° C.

3. Process according to claim 2, wherein the initial reaction is carried out at a temperature of 95°–125° C.

4. Process according to claim 1, wherein the polar, aprotic solvent employed is dimethylsulphoxide (DMSO), dimethylformamide (DMF) or dimethylsulphone ($DMSO_2$).

5. Process according to claim 4, wherein the polar, aprotic solvent employed is DMSO.

6. Process according to claim 1, wherein the alkali metal fluoride employed is potassium fluoride.

7. Process according to claim 1, wherein the polar, aprotic solvent employed is DMSO and the process is carried out at a temperature of 60° to 160° C., and at a minimum reaction time of 20 to 0.2 hours, the temperature and the time being linked by the relationship T (° C.)=A −33 log t (h), in which A assumes values of 100–137.

8. Process according to claim 1, wherein, in order to resolve the reaction mixture, the alkali metal fluoride/chloride is removed and the reaction products are then extracted from the polar, aprotic solvent with the aid of one or more straight-chain or branched open-chain or cyclic aliphatic hydrocarbons having a boiling point of at least 30° C.

9. Process according to claim 1, wherein the desired degree of residual contamination is produced only partially by converting 2,3,5,6-tetrachloronitrobenzene into 2,3,5,6-tetrachloro-fluorobenzene and/or 2,3,4,6-tetrachloro-nitrobenzene into 2,3,4,6-tetrachlorofluorobenzene, reducing the reaction products to the aniline stage, precipitating the anilines by salt formation and removing them, after reconverting the salts into the free anilines, obtaining 3,5-dichloro-2,4-difluoro-aniline by distillative separation from tetrachloro-anilines.

10. Process according to claim 1, wherein the desired degree of residual contamination is only partly produced by converting 2,3,5,6-tetrachloronitrobenzene into 2,3,5,6-tetrachloro-fluorobenzene and/or 2,3,4,6-tetrachloro-nitrobenzene into 2,3,4,6-tetrachlorofluorobenzene, reducing the reaction products to the aniline stage, precipitating the anilines by salt formation and removing them, phosgenating the aniline salts, as such or after reconversion of the salts into the free anilines, to the isocyanate stage, and obtaining 3,5-dichloro-2,4-difluoro-phenyl-isocyanate by distillative separation of tetrachloro-phenyl-isocyanates.

* * * * *